United States Patent
Collier, Jr. et al.

(10) Patent No.: US 7,763,619 B2
(45) Date of Patent: Jul. 27, 2010

(54) COMPOUNDS WITH 5-HT$_{1A}$ ACTIVITY USEFUL FOR TREATING DISORDERS OF THE OUTER RETINA

(75) Inventors: Robert J. Collier, Jr., Arlington, TX (US); Michael A. Kapin, Arlington, TX (US); Mark R. Hellberg, Highland Village, TX (US); Thomas R. Dean, Weatherford, TX (US)

(73) Assignee: Alcon, Inc., Hunenberg (CH)

( * ) Notice: Subject to any disclaimer, the term of this patent is extended or adjusted under 35 U.S.C. 154(b) by 555 days.

(21) Appl. No.: 11/187,474

(22) Filed: Jul. 22, 2005

(65) Prior Publication Data

US 2005/0256129 A1 Nov. 17, 2005

Related U.S. Application Data

(63) Continuation of application No. 10/221,070, filed as application No. PCT/US01/05700 on Feb. 23, 2001, now abandoned.

(60) Provisional application No. 60/190,279, filed on Mar. 17, 2000.

(51) Int. Cl.
A61K 31/497 (2006.01)
(52) U.S. Cl. .................. 514/252.14; 514/912
(58) Field of Classification Search ............ 514/252.14, 514/912
See application file for complete search history.

(56) References Cited

U.S. PATENT DOCUMENTS 5,578,612 A 11/1996 Macor

FOREIGN PATENT DOCUMENTS

| DE | 601 00 625 T2 | 2/2004 |
|---|---|---|
| EP | 0 352 613 B1 | 7/1989 |
| EP | 0 540 914 B1 | 10/1992 |
| EP | 0 749 970 B1 | 6/1996 |
| EP | 0 771 563 A2 | 7/1997 |
| EP | 1 263 504 B1 | 8/2003 |
| GR | 3046845 | 11/2003 |
| HK | 1051504 | 4/2004 |
| JP | 2262518 A | 10/1990 |
| JP | 3128332 A | 5/1991 |
| MX | 229125 | 7/2005 |
| WO | WO 92/02338 A1 | 11/1992 |
| WO | WO 97/35579 A1 | 9/1997 |
| WO | WO 98/18458 A1 | 5/1998 |
| WO | WO 99/26621 A1 | 6/1999 |
| WO | WO 01/34586 A2 | 5/2001 |
| WO | WO 01/34586 A3 | 5/2001 |
| ZA | 2002/6350 | 10/2003 |

OTHER PUBLICATIONS

De Vry et al., BAY x 3702, a novel aminomethylchroman derivative with potent 5-HT1A receptor agonist properties.

DeVry and Horwath, 1997, "Neuroprotectant 5-HT1A Agonist, (Bay x 3702)"; Drugs FUT 22(4): 341-349.

Gupta et al., 1994, "Therapeutic Potentials of 5-HT Receptor Modulators", Indian J of Pharmacology 26: 94-107.

Horvath et al., "Neuroprotective effect of the novel 5-HT1A receptor agonist BAY x 3702 in a rat model of permanent focal cerebral isochemia and traumatic brain injury".

Macor et al., 1992, "Synthesis and Serotonergic Pharmacology of the Enantiomers of 3-[(N-Methylpyrrolikin-2-yl)methyl]-5methoxy-1H-indole . . . ", J Med Chem 35: 4503-4505.

Newman-Tancredi et al., 1998, "Agonist and antagonist actions of antipsychotic agents as 5-HT1A receptors: a [35S]GTP•S binding study", Eur J Pharmacol 355: 245-256.

Schwarz et al, "Pharmacokinetics of the novel 5-HT1A neuroprotectant BAY x 3702 in the rat".

Abler et al., "Photic injury triggers apoptosis of photoreceptor cells," Res Commun Mol Pathol Pharmacol, vol. 92(2):177-189, May 1996.

Alessandri et al., "The neuroprotective effect of a new serotonin receptor agonist, BAY X3702, upon focal ischemic brain damage caused by acute subdural hematoma in the rat," Brain Research, vol. 845:232-235, 1999.

Berson, Eliot. L., "Retinitis Pigmentosa," Invest Ophthalmology & Visual Science, vol. 34(5):1659-1676, Apr. 1993.

Bielenberg et al., "5-Hydroxytryptamine1A agonists and a new therapeutic principal for stroke treatment," Stroke, vol. 21(12):IV161-163, Dec. 1990.

Bradford, Marion M., "A rapid and sensitive method for the quantitation of microgram quantities of protein utilizing the protein utilizing the principle of protein-dye binding," Analytical Biochemistry, vol. 72:248-254, 1976.

Bressler et al., "Age-related macular degeneration," Survey of Ophthalmology, vol. 32(6):375-413, May-Jun. 1988.

Bressler et al., "Clinicopathologic correlation of drusen and retinal pigment epithelial abnormalities in age-related macular degeneration," Retina, vol. 14:130-142, 1994.

Chidlow, et al., "The 5-HT1A receptor agonist 8-OH-DPAT lowers intraocular pressure in normotensive NZW rabbits," Exp. Eye Research, vol. 69:587-593, 1999.

(Continued)

*Primary Examiner*—Zohreh A Fay
(74) *Attorney, Agent, or Firm*—Teresa J. Schultz (57) ABSTRACT

Compositions and methods for treating disorders of the outer retina with compounds with 5-HT$_{1A}$ agonist activity are disclosed.

9 Claims, 6 Drawing Sheets

OTHER PUBLICATIONS

Chu, et al., "8OH-DPAT-Induced ocular hypotensive: sites and mechanisms of action," vol. 69:227-238, 1999.

Collier et al., "Inhibition of photo-oxidative induced retinal damage by diphenylalkylamines," Investigative Ophthalmology & Visual Science, vol. 36(4):S516, Mar. 15, 1995.

Collier et al., "Prevention of photic induced retinal injury by eliprodil," Invest Ophthalmology & Visual Science, vol. 40(4):S159, Mar. 15, 1999.

Cruickshank, et al., "Sunlight and age-related macular degeneration," Arch Ophthalmology, vol. 111:514-518, Apr. 1993.

Curcio et al., "Photoreceptor loss in age-related macular degeneration," Invest Ophthalmology & Visual Science, vol. 37(7):1236-1249, 1996.

De Vry et al., "Characterization of the aminomethylchroman derivative BAY X3702 as a highly potent 5-hydroxytryptamine1A receptor agonist," J Pharmacology & Experimental Therapeutics, vol. 284(3):1082-1094, 1998.

Edward et al., "Amelioration of light-induced retinal degeneration by a calcium overload blocker," Arch Ophthalmol., vol. 109:554-562, 1991.

Faktorovich et al., "Photoreceptor degeneration in inherited retinal dystrophy delayed by basic fibroblast growth factor," Letters to Nature, vol. 347:83-86, 1990.

Fournier et al., "Protective effects of SR 57746A in central and peripheral models of neurodegenerative disorders in rodents and primates," Neuroscience, vol. 55(3):629-641, 1993.

Fournier et al., "The effect of the nonpeptide neurotrophic compound SR 57746A on the progression of the disease state of the pmn mounse," British Journal of Pharmacology, vol. 124:811-817, 1998.

Frasson et al., "Retinitis pigmentosa: rod photoreceptor rescue by a calcium-channel blocker in the rd mouse," Nature Medicine, vol. 5(10):1183-1187, 1999.

Fu et al., "Dexamethasone ameliorates retinal photic injury in albino rats," Exp. Eye Res., vol. 54:583-594, 1992.

Ge-Zhi et al., "Apoptosis in human retinal degenerations," Tr. Am. Ophth. Soc., vol. 94, 411-430, 1996.

Green et al., "Age-related macular degeneration histopathologic studies," Ophthalmology, vol. 100 (10):1519-1535, 1993.

Green et al., "Histopathologic studies of choroidal neovascularization," Indocyanine Green Angiography, Lawrence A. Yannuzzi, M.D., Robert W. Flower, D.Sc., & Jason S. Slakter, M.D. (Eds.), St. Louis: Mosby, Chapter 11:151-156, 1997.

Green et al., "Pathologic features of senile macular degeneration," Ophthalmology, vol. 92(5):615-627, 1985.

Green, et al., "Senile macular degeneration: a histopathologic study," Tr. Am. Ophth.l Soc., vol. 75:180-254, 1977.

Heckenlively, John R., "RP Cone-rod degeneration," Tr. Am. Ophth. Soc, vol. 85:438-470, 1987.

Kozaki et al., "Light-induced retinal damage in pigmented rabbi—2. Effect of alpha-tocopherol," Nippon Ganka Gakkai Zasshi, vol. 98(10):948-954, 1994.

Lam et al., "Amelioration of retinal photic injury in albino rats by dimethylthiourea," Arch Ophthalmol., vol. 108:1751-1757, 1990.

Lam et al., "Methylprednisolone therapy in laser injury of the retina," Graefes Archive for Clinical & Experimental Ophthalmology, vol. 231:729-736, 1993.

LaVail et al., Multiple growth factors, cytokines, and neurotrophins rescue photoreceptors from the damaging effects of constant light, Proc. Natl. Acad. Sci., vol. 89:11249-11253, 1992.

Li et al., "Amelioration of photic injury in rat retina by ascorbic acid: a histopathologic study," Investigative Ophthalmology & Visual Science, vol. 26:1589-1598, 1985 (appln lists as "Organisciak").

Li et al., "Desferrioxamine ameliorates retinal photic injury in albino rats," Current Eye Research, vol. 10(2):133-144, 1991.

Li et al., "Amelioration of retinal photic injury by a combination of flunarizine and dimethylthiourea," Exp. Eye Research, vol. 56:71-78, 1993.

Lima, et al., "8-[3H]Hydroxy-2-(Di-n-Propylamino)tetralin binding sites in goldfish retina," Neurochemical Research, vol. 19(3):249-255, 1994.

Lima, et al., "Serotonin inhibits outgrowth of goldfish retina and impairs the trophic effect of taurine," Journal of Neuroscience Research, vol. 38:444-450, 1994.

Lopez-Rodriguez, et al., "Synthesis and structure-activity relationships of a new model of arylpiperazines . . . ," J Med. Chem., vol. 42:36-49, 1999.

Morin, et al., "A method to measure simultaneously cyclic AMP and inositol phosphate accumulation in rat brain slices," J Neurochemistry, vol. 56(4):1114-1120, 1991.

Naash et al., "Induced acceleration of photoreceptor degeneration transgenic mice expressing mutant rhodopsin," Invest Ophthalmology & Visual Science, vol. 37(5):775-782, 1996.

Nickells et al., "Apoptosis in ocular disease: a molecular overview," Ophthalmic Genetics, vol. 17 (4):145-165, 1996.

Noell et al., "Retinal damage by light in rats," Investigative Ophthalmology, vol. 5(5):450-472, 1966.

Oosterink et al., "Neuroprotection against N-methyl-D-aspartate-induced excitotoxicity in rat magnocellular nucleus basalis by the 5-HT1A receptor agonist 8-OH-DPAT," European Journal of Pharmacology, vol. 358:147-52, 1998.

Organisciak et al., "Protection by dimethyithiourea against retinal light damage in rats," Invest Ophthalmology & Visual Science, vol. 33:1599-1609, 1992.

Osborne, et al., "Do Beta-adrenoceptors and serotonin 5HT1A receptors have similar functions in the control of intraocular pressure in the rabbit?" Ophthalmologica, vol. 210:308-314, 1996.

Pagon, Robert, A., "Retinitis Pigmentosa," Survey of Ophthalmology, vol. 33(3):137-177, 1988.

Peruche et al., "Protective effects of 5HT1A receptor agonists against neuronal damaged demonstrated in vivo and in vitro," J Neural Transm., vol. 8:73-83, 1994.

Prehn et al., "Neuroprotective properties of 5-HT1A receptor agonists in rodent models of focal and global cerebral ischemia," European Journal of Pharmacology, vol. 203:213-222, 1991.

Prehn et al., "Effects of serotonergic drugs in experimental brain ischemia: evidence for a protective role of serotonin in cerebral ischemia," Brain Research, vol. 630(1-2):10-20, 1993.

Pruett, et al., "Retinitis pigmentosa: clinical observations and correlations," Tr. Am. Ophth. Soc., vol. 81:693-735, 1983.

Rapp et al., "Evaluation of retinal susceptibility to light damage in pigmented rats supplemented with beta-carotene," Current Eye Research, vol. 15:219-232, 1995.

Salomon, Y., "[2] cellular responsiveness to hormones and neurotransmitters: conversion of [3H] cAMP in cell monolayers, cell suspensions, and tissue slices," Methods in Enzymology, vol. 195:22-28, 1991.

Salomon, Y., "Adenylate Cyclase Assay," Advances in Cyclic Nucleotide Research, vol. 10:35-55, 1979.

Schneider et al., "Photocoagulation of well-defined choroidal neovascularization in age-related macular degeneration," Retina, vol. 18:242-250, 1998.

Schoeffter et al., "Inhibition of cAMP accumulation via recombinant human serotonin 5HT1A receptors: considerations on receptor effector coupling acoss systems," Neuropharmacology, vol. 36(4/5):429-437, 1997.

Semkova et al., "Neuroprotective effect of 5HT1A receptor agonist, BAY X3702, demonstrated in vitro and in vivo," European Journal of Pharmacology, vol. 359:251-60, 1998.

Sharif et al., "[3H]AL-5858 ([3H]9•-(+)-Fluprostenol). Carboxylic Acid of Travoprost (AL-6221), a Novel FP Prostaglandin o Study the Pharmacology and Autoradiographic Localization of the FP Receptor," J. Pharm. Pharmacol., vol. 51:685-694, 1999.

Taylor, et al., "Long-term effects of visible light o the eye," Arch Ophthalmol., vol. 110:99-104, 1992.

Urbina, et al., "5HT1A receptor agonist differentially increases cyclic AMP concentration in intact and lesioned goldfish retina. In Vitro inhibiton of outgrowth by forskolin," Neurochem., vol. 29 (5):453-460, 1996.

Wang, et al., "Effect of 5-methylurapidil, an •1a-adrenergic antagonist and 5-hydroxytryptamine1a agonist, on aqueous humor dynamics in monkeys and rabbits," Current Eye Research, vol. 16 (8):769-775, Aug. 1997.

Wang, et al., "Effect of p-MPP1 Hydrochloride (p-MPP1) Applied Before 5-methylurapidil (5-MU) on Intraocular Pressure (IOP) in Normal Monkeys," IVOS, vol. 39(S488):2236, Mar. 1998.

Young, Richard W., "Solar radiation and age-related macular degeneration," Survey of Ophthalmology, vol. 32(4):252-269, 1988.

International Search Report for PCT/US2001/05700 dated Apr. 22, 2002.

International Preliminary Examination Report for PCT/US2001/05700 dated Sep. 4, 2002.

FIGURE 1A

* Significantly higher responses compared to vehicles (p<0.05).

FIGURE 1B

* Significantly higher responses compared to vehicles ($p<0.05$).

FIGURE 2

* Significantly less damaged than vehicle (p<0.05).

FIGURE 3

* Significantly better than vehicle (p<0.05) and not different than control.

FIGURE 4A

* Significantly better response compared to vehicle (p < 0.05).

FIGURE 4B

* Significantly better response compared to vehicle ($p < 0.05$).

COMPOUNDS WITH 5-HT$_{1A}$ ACTIVITY USEFUL FOR TREATING DISORDERS OF THE OUTER RETINA

This application is a continuation of U.S. Ser. No. 10/221,070 filed Sep. 9, 2002, now abandoned which is a 371 of PCT/US01/05700 filed Feb. 23, 2001, which claims benefit of U.S. Ser. No. 60/190,279 filed Mar. 17, 2000.

The present invention is directed to compounds with 5-HT$_{1A}$ agonist activity useful for treating disorders of the outer retina resulting from acute or chronic degenerative conditions or diseases of the eye.

BACKGROUND OF THE INVENTION

Age-related macular degeneration (AMD) is the leading cause of blindness in the elderly, with an incidence of about 20% in adults 65 years of age increasing to 37% in individuals 75 years or older. Non-exudative AMD is characterized by drusen accumulation and atrophy of rod and cone photoreceptors in the outer retina, retinal pigment epithelium (RPE), Bruch's membrane and choriocapillaris; while exudative AMD leads to choroidal neovascularization (Green and Enger, *Ophthalmol*, 100:1519-35, 1993; Green et al., *Ophthalmol*, 92:615-27, 1985; Green and Key, *Trans Am Ophthalmol Soc*, 75:180-254, 1977; Bressler et al., *Retina*, 14:130-42, 1994; Schneider et al., *Retina*, 18:242-50, 1998; Green and Kuchle (1997). In: Yannuzzi, L. A., Flower, R. W., Slakter, J. S. (Eds.) *Indocyanine green angiography*. St. Louis: Mosby, p. 151-6). Retinitis pigmentosa (RP) represents a group of hereditary dystrophies characterized by rod degeneration with secondary atrophy of cone photoreceptors and underlying pigment epithelium. (Pruett, *Trans Am Ophthalmol Soc*, 81:693-735, 1983; Heckenlively, *Trans Am Ophthalmol Soc*, 85:438-470, 1987; Pagon, *Sur Ophthalmol*, 33:137-177, 1988; Berson, *Invest Ophthalmol Vis Sci*, 34:1659-1676, 1993; Nickells and Zack, *Ophthalmic Genet*, 17:145-65, 1996). The pathogenesis of retinal degenerative diseases such as AMD and RP is multifaceted and can be triggered by environmental factors in normal individuals or in those who are genetically predisposed. To date more than 100 genes have been mapped or cloned that may be associated with various outer retinal degenerations.

Light exposure is an environmental factor that has been identified as a contributing factor to the progression of retinal degenerative disorders such as AMD (Young, *Sur Ophthal*, 32:252-269, 1988; Taylor, et al., *Arch Ophthal*, 110:99-104, 1992; Cruickshank, et al., *Arch Ophthal*, 111:514-518, 1993). Photo-oxidative stress leading to light damage to retinal cells has been shown to be a useful model for studying retinal degenerative diseases for the following reasons: damage is primarily to the photoreceptors and retinal pigment epithelium (RPE) of the outer retina, the same cells that are affected in heredodegenerative diseases (Noell et al., *Invest Ophthal Vis Sci*, 5, 450-472, 1966; Bressler et al., *Sur Ophthal*, 32, 375-413, 1988; Curcio et al., *Invest Ophthal Vis Sci*, 37, 1236-1249, 1996); apoptosis is the cell death mechanism by which photoreceptor and RPE cells are lost in AMD and RP, as well as following a photo-oxidative induced cell injury (Ge-Zhi et al., *Trans AM Ophthal Soc*, 94, 411-430, 1996; Abler et al., *Res Commun Mol Pathol Pharmacol*, 92, 177-189, 1996; Nickells and Zack, *Ophthalmic Genet*, 17:145-65, 1996); light has been implicated as an environmental risk factor for progression of AMD and RP (Taylor et al., *Arch Ophthalmol*, 110, 99-104, 1992; Naash et al., *Invest Ophthal Vis Sci*, 37, 775-782, 1996); and therapeutic interventions which inhibit photo-oxidative injury have also been shown to be effective in animal models of heredodegenerative retinal disease (LaVail et al., *Proc Nat Acad Sci*, 89, 11249-11253, 1992; Fakforovich et al., *Nature*, 347, 83-86, 1990; Frasson et al., *Nat. Med.* 5, 1183-1187, 1990).

A number of different compound classes have been identified in various animal models that minimize retinal photo-oxidative injury. They include: antioxidants such as ascorbate (Organisciak et al., *Invest Ophthal Vis Sci*, 26:1589-1598, 1985), dimethylthiourea (Organisciak et al., *Invest Ophthal Vis Sci*, 33:1599-1609, 1992; Lam et al., *Arch Ophthal*, 108:1751-1752, 1990), α-tocopherol (Kozaki et al., *Nippon Ganka Gakkai Zasshi*, 98:948-954, 1994) and β-carotene (Rapp et al., *Cur Eye Res*, 15:219-232, 1995); calcium antagonists such as flunarizine (Li et al., *Exp Eye Res*, 56: 71-78, 1993; Edward et al., *Arch Ophthal*, 109, 554-622, 1992; Collier et al., *Invest Ophthal Vis Sci*, 36:S516); growth factors such as basic-fibroblast growth factor, brain derived nerve factor, ciliary neurotrophic factor, and interleukin-1-β (LaVail et al., *Proc Nat Acad Sci*, 89, 11249-11253, 1992); glucocorticoids such as methylprednisolone (Lam et al., *Graefes Arch Clin Exp Ophthal*, 231, 729-736, 1993) and dexamethasone (Fu et al., *Exp Eye Res*, 54, 583-594, 1992); iron chelators such as desferrioxamine (Li et al., *Cur Eye Res*, 2, 133-144, 1991); NMDA-antagonists such as eliprodil and MK-801 (Collier et al., *Invest Ophthal Vis Sci*, 40:S159, 1999).

Serotonergic 5-HT$_{1A}$ agonists (i.e., buspirone, ziprasidone, urapidil) have either been registered or launched for the treatment of anxiety, hypertension, schidzophrenia, psychosis or depression-bipolar disorders. In addition, 5-HT$_{1A}$ agonists have been shown to be neuroprotective in various animal models and are being evaluated in the clinic to treat cerebral ischemia, head trauma, Alzheimer's Disease, Multiple Sclerosis and amytrophic lateral sclerosis. The 5-HT$_{1A}$ agonists, 8-OH-DPAT (8-hydroxy-2-(di-n-propylamino)tetralin) and ipsapirone, were shown to prevent NMDA-induced excitotoxic neuronal damage in the rat magnocellular nucleus basalis (Oosterink et al., *Eur J Pharmacol*, 358:147-52, 1998), dosing with Bay-x-3702 significantly reduced ischemic damage in a rat acute subdermal hematoma model (Alessandri et al., *Brain Res*, 845:232-5, 1999), while 8-OH-DPAT, Bay-x-3702, urapidil, gepirone and CM 57493 significantly reduced cortical infarct volume in the rat (Bielenberg and Burkhardt, *Stroke*, 21(Suppl): IV161-3; Semkova et al., *Eur J Pharmacol*, 359:251-60, 1998; Peruche et al., *J Neural Transm—Park Dis Dement Sect*, 8:73-83, 1994) and mouse (Prehn et al., *Eur J Pharmacol*, 203:213-22, 1991; Prehn et al., *Brain Res*, 630:10-20, 1993) after occlusion of the middle cerebral artery. In addition, treatment of rats with SR 57746A, a potent 5-HT$_{1A}$ agonist, has been shown to be neuroprotective following 4-vessel transient global ischemia, vincristine sulphate induced septohippocampal lesions, acrylamide-induced peripheral neuropathy, and sciatic nerve crush (Fournier et al., *Neurosci*, 55:629-41, 1993) and has been shown to delay the progression of motor neuron degeneration in pmn mice (Fournier et al., *Br J Pharmacol*, 124:811-7, 1998).

This class of compounds has been disclosed for the treatment of glaucoma (lowering and controlling IOP), see e.g., WO 98/18458 (DeSantis, et al) and EP 0771563A2 (Mano, et al.). Osborne, et al. (*Ophthalmologica*, Vol. 210:308-314, 1996) teach that 8-hydroxydipropylaminotetralin (8-OH-DPAT) (a 5-HT$_{1A}$ agonist) reduces IOP in rabbits. Wang, et al. (*Current Eye Research*, Vol. 16(8):769-775, August 1997, and IVOS, Vol. 39(4), S488, March, 1998) disclose that 5-methylurapidil, an α$_{1A}$ antagonist and 5-HT$_{1A}$ agonist lowers IOP in the monkey, but due to its α$_{1A}$ receptor activity. Also, 5-HT$_{1A}$ antagonists are disclosed as being useful for the treatment of glaucoma (elevated IOP) (e.g. WO 92/0338, McLees). Furthermore, DeSai, et al. (WO 97/35579) and Macor, et al. (U.S. Pat. No. 5,578,612) disclose the use of 5-HT$_1$ and 5-HT$_{1-like}$ agonists for the treatment of glaucoma (elevated IOP). These anti-migraine compounds are 5-HT$_{1B,D,E,F}$ agonists, e.g., sumatriptan and naratriptan and related compounds.

SUMMARY OF THE INVENTION

The present invention is directed to 5-HT$_{1A}$ agonists which have been discovered to be useful in treating disorders of the outer retina, particularly: AMD; RP and other forms of heredodegenerative retinal disease; retinal detachment and tears; macular pucker; ischemia affecting the outer retina; diabetic retinopathy; damage associated with laser therapy (grid, focal, and panretinal) including photodynamic therapy (PDT); trauma; surgical (retinal translocation, subretinal surgery, or vitrectomy) or light-induced iatrogenic retinopathy; and preservation of retinal transplants.

DESCRIPTION OF PREFERRED EMBODIMENTS

Serotonergic 5-HT$_{1A}$ agonists have been shown to be potent neuroprotective agents following varying insults to the central nervous system. Unexpectedly, we have demonstrated that 8-OH-DPAT (8-hydroxy-2-(di-n-propylamino)tetralin), buspirone and SR-57746A exhibit potent neuroprotective activity in the retina and prevent light-induced apoptotic cell death to photoreceptors and RPE cells. We have found that treatment with buspirone can completely prevent photo-oxidative induced retinopathy and significantly reduce loss of retinal DNA and ONL thinning. The safety advantages of some of these compounds make them particularly desirable for both acute and chronic therapies. Such an agent would have utility in the treatment of various outer retinal degenerative diseases.

In our light damage paradigms, antioxidants were either ineffective (α-tocopherol) or marginally effective at high doses (ascorbate, vitamin E analogs). Similarly, some calcium antagonists (flunarizine, nicardipine) were moderately effective while others (nifedipine, nimodipine, verapamil) had no effect in preventing light-induced functional or morphological changes. However, it has been discovered that 5-HT$_{1A}$ agonists are 100-fold more potent in these light damage paradigms and therefore are useful for treating disorders of the outer retina.

The invention contemplates the use of any pharmaceutically acceptable 5-HT$_{1A}$ agonist, including pharmaceutically acceptable salts, for treating disorders of the outer retina (Compounds). Pharmaceutically acceptable means the Compounds can be safely used for the treatment of diseases of the outer retina. As used herein, the outer retina includes the RPE, photoreceptors, Muller cells (to the extent that their processes extend into the outer retina), and the outer plexiform layer. The compounds are formulated for systemic or local ocular delivery.

Disorders of the outer retina encompass acute and chronic environmentally induced (trauma, ischemia, photo-oxidative stress) degenerative conditions of the photoreceptors and RPE cells in normal or genetically predisposed individuals. This would include, but not limited to, AMD, RP and other forms of heredodegenerative retinal disease, retinal detachment, tears, macular pucker, ischemia affecting the outer retina, diabetic retinopathy, damage associated with laser therapy (grid, focal and panretinal) including photodynamic therapy (PDT), thermal or cryotherapy, trauma, surgical (retinal translocation, subretinal surgery or vitrectomy) or light induced iatrogenic retinopathy and preservation of retinal transplants.

Compounds of the present invention have potent affinity for 5-HT$_{1A}$ receptors with IC$_{50}$ values that range up to about 500 nM (preferably less than 100 nM). These Compounds are also either full or partial agonists with IC$_{50}$ values ranging up to about 1 μM (preferably less than 500 nM). Representative 5-HT$_{1A}$ agonists useful according to the present invention include, but are not limited to: tandospirone, urapidil, ziprasidone, repinotan hydrochloride, xaliproden hydrochloride (SR-57746A), buspirone, flesinoxan, 5-{4-[4-(5-cyano-3-indolyl)-butyl]-1-piperazinyl}-benzofuran-2-carboxamide (EMD-68843), 7-[4-[(3-phenylphenyl)methyl]piperazin-1-yl]-3H-benzooxazol-2-one (bifeprunox mesylate; DU-127090), gepirone, alnespirone, (R)-5,6-dihydro-5-(methylamino)-4H-imidazo[4,5,1-ij]quinolin-2-butenedioate maleate (PNU-95666), [N-piperonyl-2-amino-1,2,3,4-tetrahydrobenzo(b)thieno(2,3-c)pyridine]-3-carbamide hydrochloride (AP-521), flibanserin, 5-{3-[((2S)-1,4-benzodioxan-2-ylmethyl)amino]propoxy}-1,3-benzodioxole HCl (MKC-242), lesopitron, sarizotan hydrochloride, 1-(4-trifluoromethyl-2-pyridinyl)-4-[4-[2-oxo-1-pyrrolidinyl]butyl]piperazine (E)-2-butenedioate (Org-13011), Org-12966, 4-(4-fluorophenil)-1,2,3,6-tentrahydro-1-[4-(1,2,4-triazol-1-il)butyl]pyridine citrate (E-5842), 3-chloro-4-[4-[4-(2-pyridinyl)-1,2,3,6-tetrahydropyridin-1-yl]butyl]-1,4-benzoxazepin-5 (4H)-one (SUN-N4057), and 8-OH-DPAT.

Receptor binding and agonist activity according to this invention can be determined using the following methods.

Method 1

5-HT$_{1A}$ Receptor Binding Assay

5-HT$_{1A}$ binding studies were performed with human cloned receptors expressed in Chinese hamster ovary (CHO) cells using ($^3$H)8-OH DPAT as the ligand. Membranes from Chinese hamster ovary cells (CHO) expressing cloned 5-HT$_{1A}$ receptors (manufactured for NEN by Biosignal, Inc., Montreal, Canada) were homogenized in approximately 40 volumes of 50 mM Tris pH 7.4 for 5 sec. Drug dilutions were made using a Beckman Biomek 2000 robot (Beckman Instruments, Fullerton, Calif.). Incubations were conducted with membrane prep, test compounds, and 0.25 nM [$^3$H]8-OH-DPAT (NEN, Boston, Mass.) in the same buffer at 27° C. for 1 h. Assays were terminated by rapid vacuum filtration over Whatman GF/B glass fiber filters pre-soaked in 0.3% polyethyleneimine. Bound radioactivity was measured using liquid scintillation spectrometry. Data were analyzed using non-linear curve fitting programs (Sharif et al., J Pharmac Pharmacol, 51: 685-694, 1999).

Ligand binding studies can also be run using membrane preparations from calf and rat brain (local source) and human cortex membranes. Specific brain regions were dissected out, homogenized in 10 volumes of 0.32 M sucrose and centrifuged for 10 min at 700×g. The resulting supernatant was centrifuged at 43,500×g for 10 min and the pellet re-suspended in 50 mM Tris-HCl (pH 7.7, 25° C.) using a 10 sec polytron treatment. Aliquots were stored at −140° C. To remove endogenous serotonin, the preps were incubated at 37° C. for 10 min prior to the experiment. Assay incubations were terminated by rapid filtration over Whatman GF/C filters using a Brandel cell harvester. $K_i$ values were calculated using the Cheng-Prusoff equation (De Vry et al., J Pharm Exper Ther, 284:1082-1094, 1998.)

Method 2

5-$HT_{1A}$ Functional Assays

The function of Compounds of the present invention can be determined using a variety of methods to assess the functional activity of 5-$HT_{1A}$ agonists. One such assay is performed using hippocampal slices from male Sprague-Dawley rats, measuring the inhibition of forskolin-stimated adenylate cyclase (J Med Chem, 42:36, 1999; J Neurochem, 56:1114, 1991; J Pharm Exper Ther, 284:1082, 1998). Rat hippocampal membranes were homogenized in 25 volumes of 0.3 M sucrose containing 1 mM EGTA, 5 mM EDTA, 5 mM dithiothreitol, and 20 mM Tris-HCl, pH 7.4 at 25° C. The homogenate was centrifuged for 10 m in at 1,000×g. The supernatant subsequently was centrifuged at 39,000×g for 10 min. The resulting pellet was re-suspended in homogenization buffer at a protein concentration of approximately 1 mg/ml and aliquots were stored at −140° C. Prior to use, the membranes were rehomogenized in a Potter-Elvehjem homogenizer. Fifty µl of the membrane suspension (50 µg protein) were added to an incubation buffer containing 100 mM NaCl, 2 mM magnesium acetate, 0.2 mM ATP, 1 mM cAMP, 0.01 mM GTP, 0.01 mM forskolin, 80 mM Tris-HCl, 5 mM creatine phosphate, 0.8 U/µl creatine phosphokinase, 0.1 mM IBMX, 1-2 µCi α-[$^{32}$P]ATP. Incubations with test compounds (10 min at 30° C.) were initiated by the addition of the membrane solution to the incubation mixture (prewarmed 5 min at 30° C.). [$^{32}$P]cAMP was measured according to the method of Salomon (Adv Cyclic Nucleotide Res, 10:35-55, 1979). Protein was measured using the Bradford (Anal Biochem, 72:248-254, 1976) assay.

Functional activity can also be determined in recombinant human receptors according to the method of Schoeffter et al. (Neuropharm, 36:429-437, 1997). HeLa cells transfected with recombinant human 5-$HT_{1A}$ receptors were grown to confluence in 24-well plates. The cells were rinsed with 1 ml of Hepes-buffered saline (in mM) NaCl 130, KCl 5.4, $CaCl_2$ 1.8, $MgSO_4$ 0.8, $NaH_2PO_4$ 0.9, glucose 25, Hepes 20, pH 7.4, and phenol red 5 mg/l. The cells were labelled with 6 µCi/ml of [$^3$H]adenine (23 Ci/mmol, Amersham, Rahn A G, Zurich, Switzerland) in 0.5 ml of saline at 37° C. for 2 hr. The plates were subsequently rinsed twice with 1 ml of buffered saline containing 1 mM isobutylmethylxanthine. The cells were incubated for 15 min in 1 ml of this solution (37° C.) in the presence or absence of 10 µM forskolin and the test compound. The buffer was then removed and 1 ml of 5% trichloroacetic acid (TCA) containing 0.1 mM cAMP and 0.1 mM ATP was added to extract the samples. After 30 min at 4° C., the TCA extracts were subjected to chromatographic separation on Dowex AG 50W-X4 and alumina columns (Salomon, Meth Enzymol, 195: 22-28, 1991). Cyclic AMP production was calculated as the ratio [$^3$H]cAMP/([$^3$H]cAMP+[$^3$H]ATP).

The above procedures described in Methods 1 and 2 were used to generate the following data.

TABLE 1

5-$HT_{1A}$ Receptor Binding and Functional Assay Data.

| Compound | Receptor Binding ($IC_{50}$ nM, SEM) | cAMP Inhibition ($EC_{50}$) |
|---|---|---|
| (R,S) 8-OH-DPAT | 1.5 nM | 4.7 nM |
| (R) 8-OH-DPAT | 0.5 nM | 2.6 nM |
| SR-57746A | 2.5 nM | 3.7 nM |

In general, for degenerative diseases, the 5-$HT_{1A}$ agonists of this invention are administered orally with daily dosage of these compounds ranging between about 0.001 and about 500 milligrams. The preferred total daily dose ranges between about 1 and about 100 milligrams. Non-oral administration, such as, intravitreal, topical ocular, transdermal patch, subdermal, parenteral, intraocular, subconjunctival, or retrobulbar or subtenon's injection, trans scleral (including iontophoresis), or slow release biodegradable polymers or liposomes may require an adjustment of the total daily dose necessary to provide a therapeutically effective amount of the compound. The 5-$HT_{1A}$ agonists can also be delivered in ocular irrigating solutions. Concentrations should range from about 0.001 µM to about 100 µM, preferably about 0.01 µM to about 5 µM.

The 5-$HT_{1A}$ agonists can be incorporated into various types of ophthalmic formulations for delivery to the eye (e.g., topically, intracamerally, or via an implant). They may be combined with ophthalmologically acceptable preservatives, surfactants, viscosity enhancers, gelling agents, penetration enhancers, buffers, sodium chloride, and water to form aqueous, sterile ophthalmic suspensions or solutions or preformed gels or gels formed in situ. Ophthalmic solution formulations may be prepared by dissolving the compound in a physiologically acceptable isotonic aqueous buffer. Further, the ophthalmic solution may include an ophthalmologically acceptable surfactant to assist in dissolving the compound. The ophthalmic solutions may contain a viscosity enhancer, such as, hydroxymethylcellulose, hydroxyethylcellulose, hydroxypropylmethylcellulose, methylcellulose, polyvinyl-pyrrolidone, or the like, to improve the retention of the formulation in the conjunctival sac. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-940, or the like, according to the published formulations for analogous ophthalmic preparations; preservatives and tonicity agents can be incorporated.

If dosed topically, the 5-$HT_{1A}$ agonists are preferably formulated as topical ophthalmic suspensions or solutions, with a pH of about 4 to 8. The 5-$HT_{1A}$ agonists will normally be contained in these formulations in an amount 0.001% to 5% by weight, but preferably in an amount of 0.01% to 2% by weight. Thus, for topical presentation, 1 to 2 drops of these formulations would be delivered to the surface of the eye 1 to 4 times per day according to the discretion of a skilled clinician.

The following topical ophthalmaic formulations are useful according to the present invention administered 1-4 times per day according to the discretion of a skilled clinician.

EXAMPLE 1

| Ingredients | Amount (wt %) |
|---|---|
| Buspirone | 0.01–2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 2

| Ingredients | Amount (wt %) |
|---|---|
| Buspirone | 0.01–2% |
| Methyl cellulose | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 3

| Ingredients | Amount (wt %) |
|---|---|
| Compound | 0.01–2% |
| Guar gum | 0.4–6.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 4

| Ingredients | Amount (wt %) |
|---|---|
| Xaliproden hydrochloride | 0.01–2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |

EXAMPLE 5

| 10 mM IV Solution w/v % | |
|---|---|
| Buspirone | 0.384% |
| L-Tartaric acid | 2.31% |
| Sodium hydroxide | pH 3.8 |
| Hydrochloric acid | pH 3.8 |
| Purified water | q.s. 100% |

EXAMPLE 6

| | 5 mg Capsules |
|---|---|
| Ingredient | mg/capsule (Total Wt. 22a mg) |
| Buspirone Hydrochloride | 5 |
| Lactose, anhydrous | 55.7 |
| Strach, Sodium carboxy-methyl | 8 |
| Cellulose, microcrystalline | 30 |
| Colloidal silicon dioxide | .5 |
| Magnesium sterage | .8 |

Method 3

Neuroprotective Effects in the Rat Photo-Oxidative Induced Retinopathy Model

The retinal protective effect of these $5\text{-HT}_{1A}$ agonists were evaluated in our photo-oxidative induced retinopathy paradigm.

Induction of Photochemical Lesion. Photochemical lesions were induced in dark adapted rats (24 hour) by exposure to (220 fc) blue light (half-amplitude bandpass=435-475 nm) for 6 hours. Animals were allowed to recover for 5 days in darkness prior to electrodiagnostic evaluation of retinal function. Rats were single housed in clear polycarbonate cages during this light exposure.

Electrodiagnostic Evaluation. The electroretinogram (ERG) was recorded from anesthetized rats after a 24-hour dark-adaptation period. Rats were anesthetized by IP injection with Ketamine-HCl (75 mg/Kg) and Xylazine (6 mg/Kg). Flash ERGs recorded from a platinum-iridium wire loop electrode positioned on the cornea were elicited by viewing a ganzfeld. Electrical responses to a series of light flashes increasing in intensity were digitized to analyze temporal characteristics of the waveform and response voltage-log intensity (VlogI) relationship. Changes in the ERG a-wave are associated with photoreceptor and retinal pigment epithelium damage while damage to the inner retina is reflected in changes in the ERG b-wave.

Assessment of Retinal Morphology. Ocular tissues were obtained from control and drug or vehicle dosed rats and fixed by immersion into a mixture of 2% paraformaldehyde and 2% glutaraldehyde. Fixed eyeballs were dehydrated in an ascending ethanol series, embedded in JB-4 plastic resin, and 1 to 1.5-micron thick sections were analyzed using a quantitative computer image analysis system attached to the microscope. Retinal layer thickness (retinal pigment epithelium, RPE; outer nuclear layer thickness, ONL; inner nuclear layer thickness, INL; and length of photoreceptor inner and outer segments, IS+OS) was measured.

Assessment of DNA Changes. Albino rats were euthanized by $CO_2$ inhalation and individual retinas were frozen in separate tubes. Each retina had been sonicated in 0.8 ml (2.0 M NaCl, 50 mM $NaPO_4$, pH 7.4, 2 mM EDTA) to yield a uniform homogenate, and stored frozen. Aliquots (0.1 ml) of each sample were diluted 10-fold with 2.0 M NaCl, 50 mM $NaPO_4$. pH 7.4, 2 mM EDTA containing 1.1 µg/ml bisbenzimidazole (Hoechst 33258). A standard curve was constructed using calf thymus DNA from 0 to 25 µg/ml in the same buffer. Triplicate 0.2 ml aliquots of each retina sample and standard were pipetted into a 96 well plate for fluorescence measurements in the Cytofluor II. The excitation wavelength was 360 nm, and the emission wavelength was 460 nm.

Subjects and Dosing. Male Sprague Dawley rats were randomly assigned to drug and vehicle experimental groups. Control rats were housed in their home cage under normal cyclic light exposure. All rats were dosed 48, 24 and 0 hours prior to a 6-hour blue-light exposure. Dosing was as follows:

1.) 8-OH-DPAT (8-hydroxy-2-(di-n-propylamino)tetralin): Rats receiving either vehicle (N=10) or 8-OH-DPAT (0.5 mg/kg [N=5] or 1.0 mg/kg [N=10]) were given three subcutaneous (SC) injections prior to light exposure. Five rats were used as controls. Retinal protection was assessed by analyzing the ERG response and measuring changes in retinal morphology.

2.) Buspirone: For DNA quantitation, six rats per treatment group were dosed IP with vehicle or buspirone (0.5 and 1 mg/kg) prior to light exposure. Retinas from seven normal rats were used as controls. To evaluate changes in retinal morphology, rats were dosed (IP) with either vehicle (N=8) or buspirone (1.0 mg/kg [N=9]). Six rats were used as controls. Retinal protection was assessed by quantitating changes in retinal DNA and measuring changes in retinal morphology.

3.) SR-57746A: Rats were dosed (IP) with vehicle (N=15) or SR-57746A (0.5 mg/kg [N=5] or 1 mg/kg [N=15]). Eleven rats were used as controls. The ERG was analyzed after a 5-day recovery period to assess retinal protection.

Figure 1A:
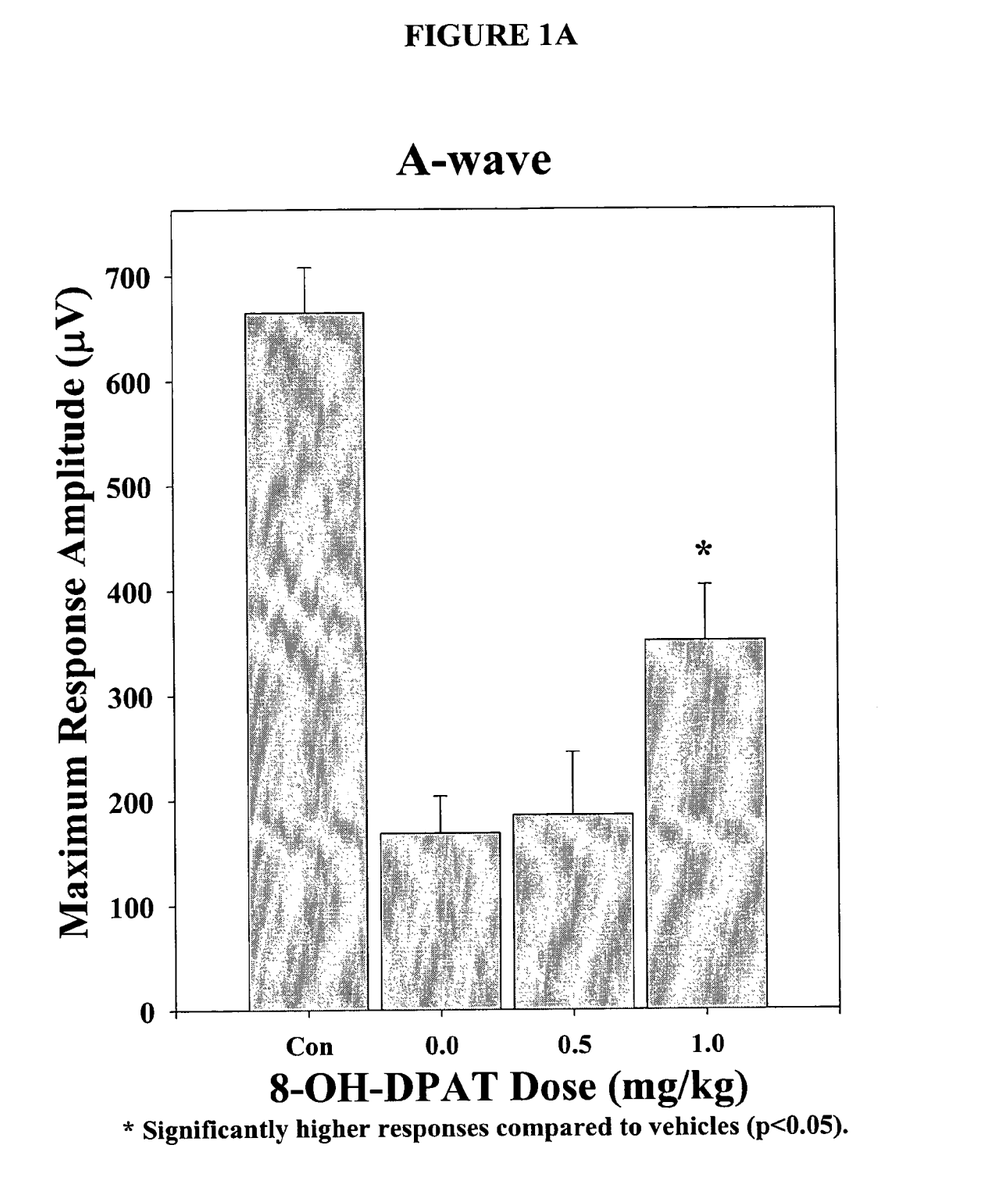
FIGS. 1A and 1B show the preservation of the ERG a- and b-wave function in rats dosed systemically with 8-OH-DPAT and exposed to a severe photo-oxidative insult.
Figure 1B:
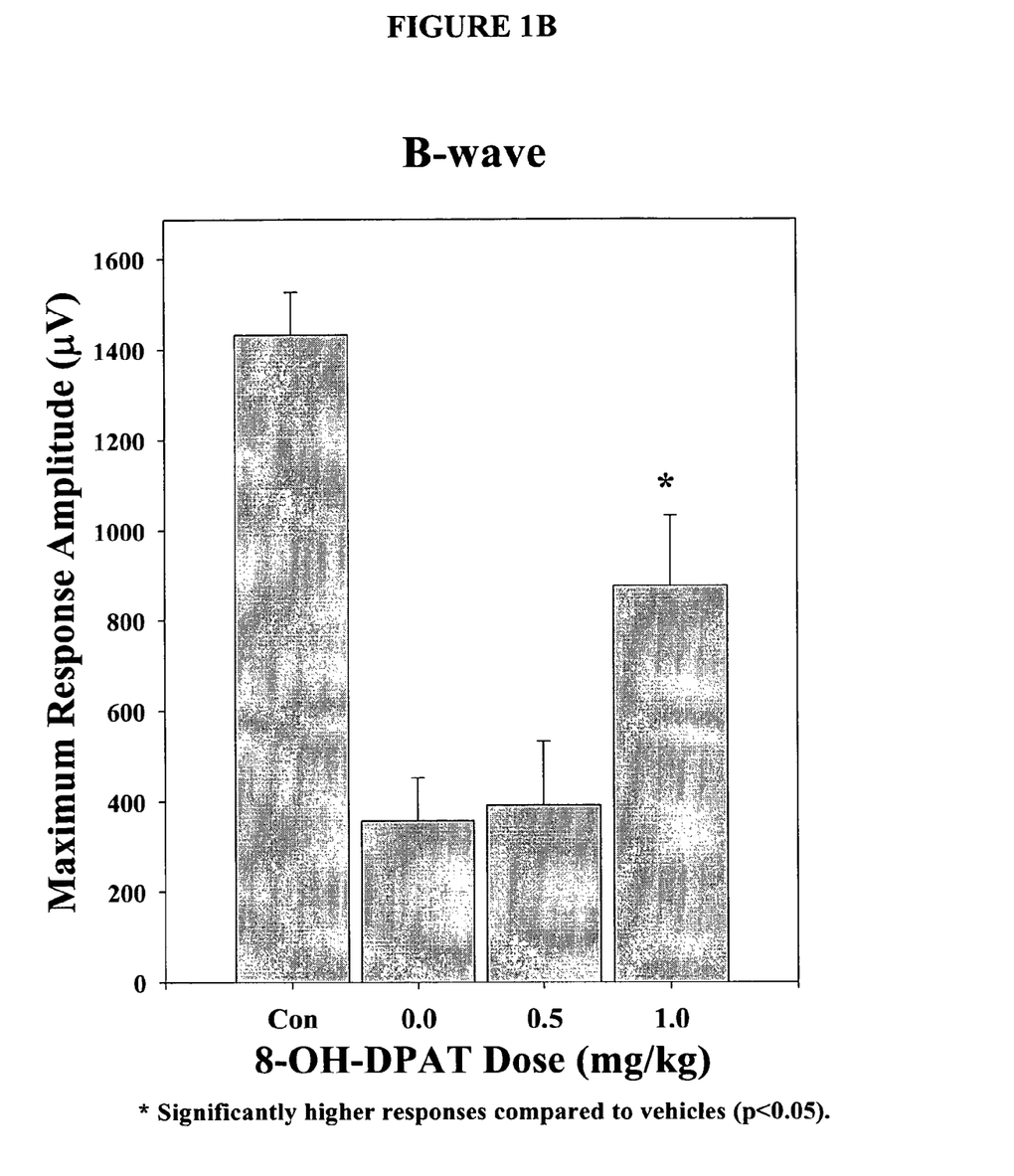

8-OH-DPAT Evaluation Results. Blue-light exposure for 6 hours resulted in a significant diminution of the ERG response amplitude (ANOVA, p<0.001; Bonferroni t-test, p<0.05) compared to normals when measured after a 5-day recovery period (FIGS. 1A and B). Blue-light exposure resulted in a 75% reduction in the maximum a- and b-wave amplitudes in vehicle dosed rats compared to controls. In addition, threshold responses were lower and evoked at brighter flash intensities.

Rats dosed with 8-OH-DPAT showed dose-dependent protection of outer and inner retina function against this photo-oxidative induced retinopathy (FIGS. 1A and B). Maximum a- and b-wave response amplitudes in 8-OH-DPAT (0.5 mg/kg) dosed rats were not different than vehicle dosed rats and were approximately 27% of control amplitudes. However, maximum a- and b-wave response amplitudes from 8-OH-DPAT (1.0 mg/kg) dosed rats were approximately 53% and 61% of normal, respectively, and significantly higher than responses measured in vehicle dosed rats (FIGS. 1A and 1B).

Figure 2:
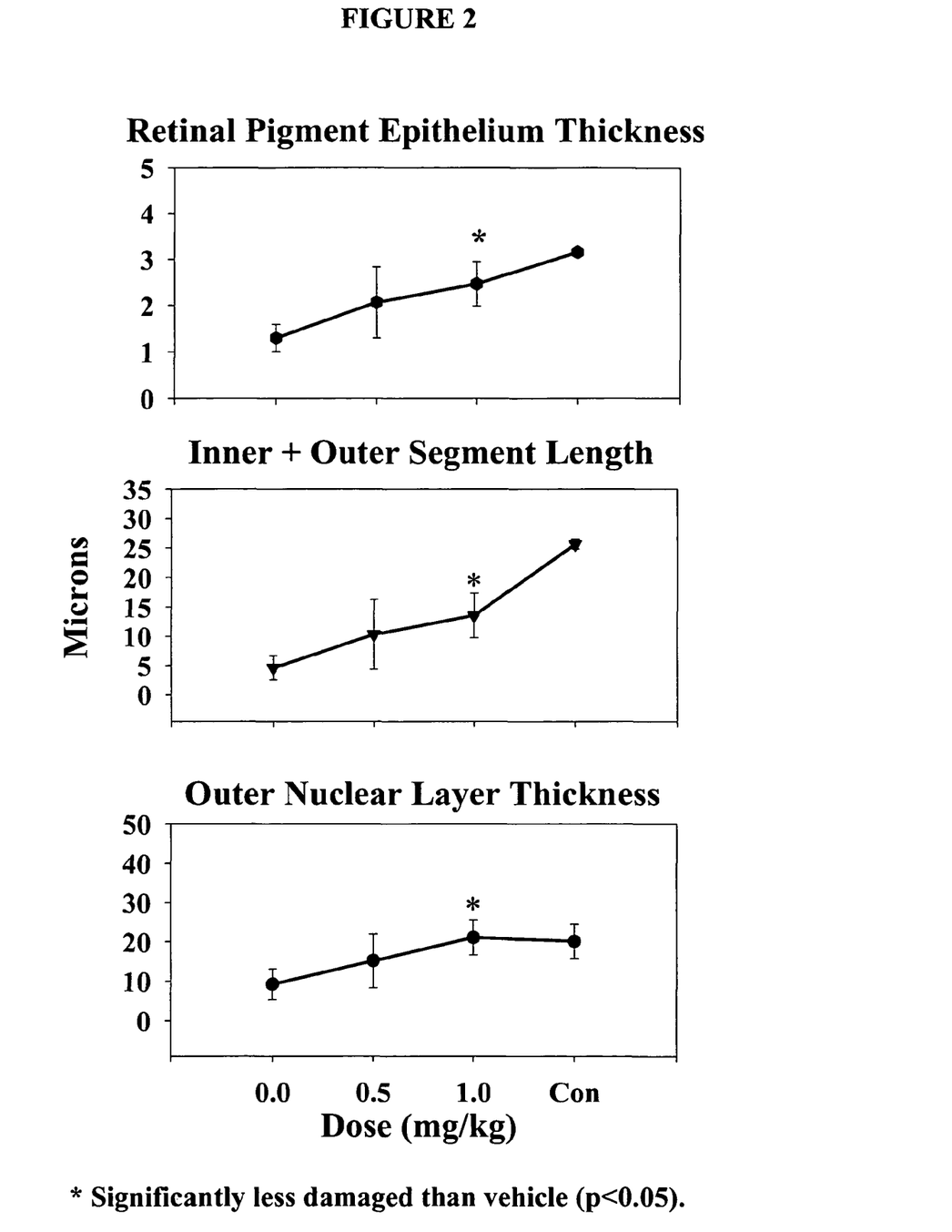
FIG. 2 shows protection of retinal morphology (photoreceptors and RPE) in rats dosed systemically with 8-OH-DPAT and exposed to a severe photo-oxidative insult.

Consistent with these ERG changes, morphometric analysis of these retinas after a 3-week recovery period demonstrated a significant (ANOVA, p<0.01) loss of photoreceptor cells, shortening of photoreceptor inner+outer segment length, and flattening of the RPE in vehicle dosed animals. No significant changes in the thickness of the INL were detected. ONL thickness was reduced 73%, inner+outer segment length was reduced 82%, and RPE thickness was reduced 59% compared to controls (FIG. 2). Lesions observed in rats dosed with 8-OH-DPAT (0.5 mg/kg) were not significantly different than lesions measured in vehicle dosed rats. While ERGs were reduced approximately 63%, the ONL thickness was reduced by 53%, photoreceptor segment length was reduced 60%, and the RPE thickness was reduced 34%. However, photic lesions observed in rats dosed with 8-OH-DPAT (1.0 mg/kg) were significantly different from vehicle dosed rats. While ERG response amplitudes were greater than 50% of normal, the ONL thickness was 2.4 fold thicker, photoreceptor segment length was 2.9 times longer, and RPE thickness was 1.9 times thicker compared to vehicle dosed rats.

Figure 3:
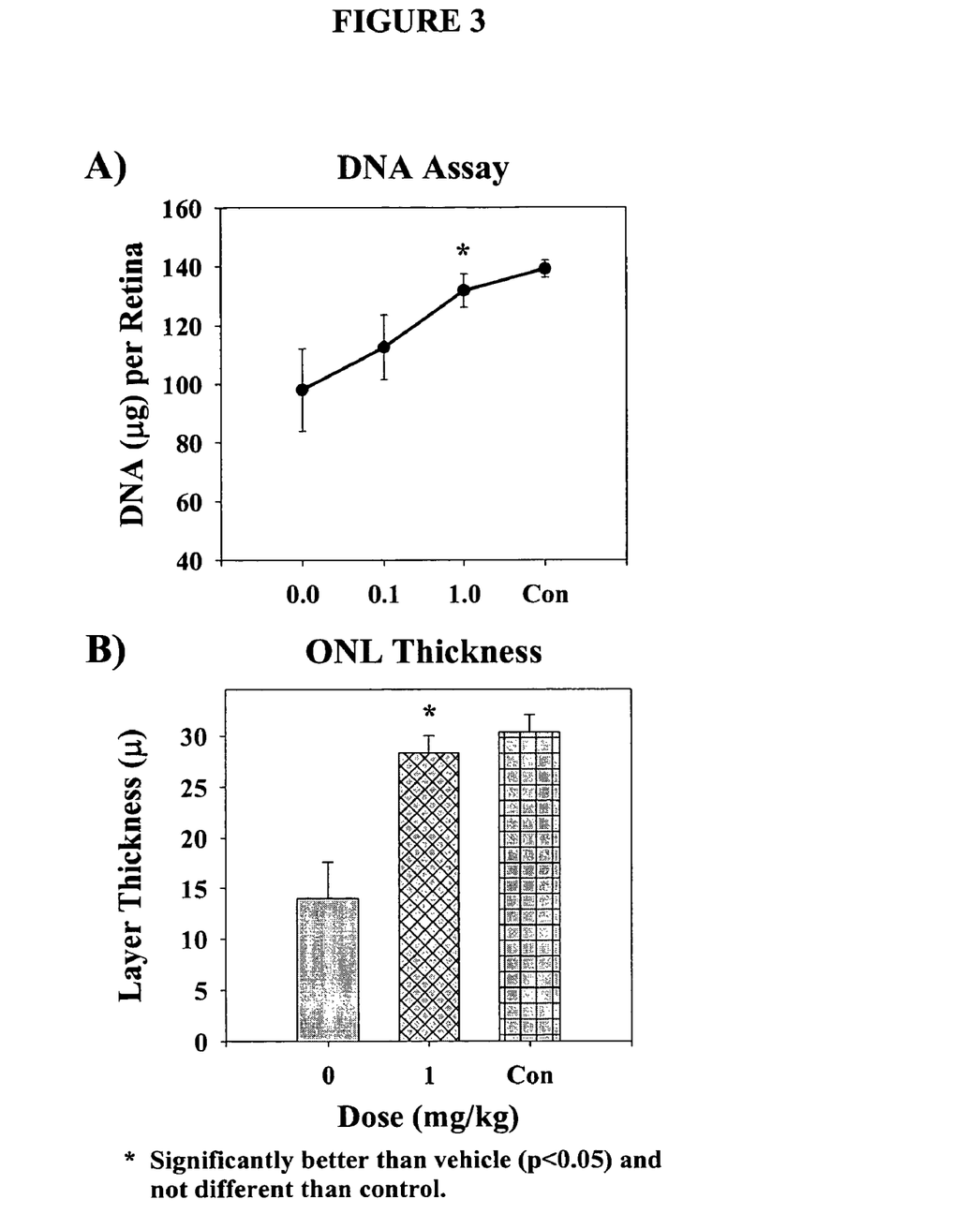
FIG. 3 shows protection of retinal DNA, a measure of retinal cell number (A), and complete protection of retinal morphology (photoreceptors) in rats dosed systemically with buspirone and exposed to a severe photo-oxidative insult.

Buspirone Evaluation Results. As seen in FIG. 3A, vehicle dosed retinal DNA levels were significantly reduced (ANOVA, p=0.017) about 30% from control levels. No significant differences were measured between groups dosed with vehicle or 0.1 mg/kg buspirone. Retinal protection was measured in rats dosed with buspirone (1 mg/kg). Retinal DNA levels were significantly higher than measured in vehicle dosed rats, but not significantly different than controls.

Blue-light exposure for 6 hours resulted in a significant reduction in photoreceptor number (ANOVA, p<0.05). Morphometric analysis of these retinas after a 4-week recovery period demonstrated a 54% thinning of the outer nuclear layer in vehicle dosed rats compared to controls (FIG. 3B). However, no significant difference in ONL thickness was measured between normal and buspirone treated rats. In rats dosed with buspirone (1 mg/kg) the ONL thickness was 28.3µ compared to 30.4µ in normal rats.

Figure 4A:
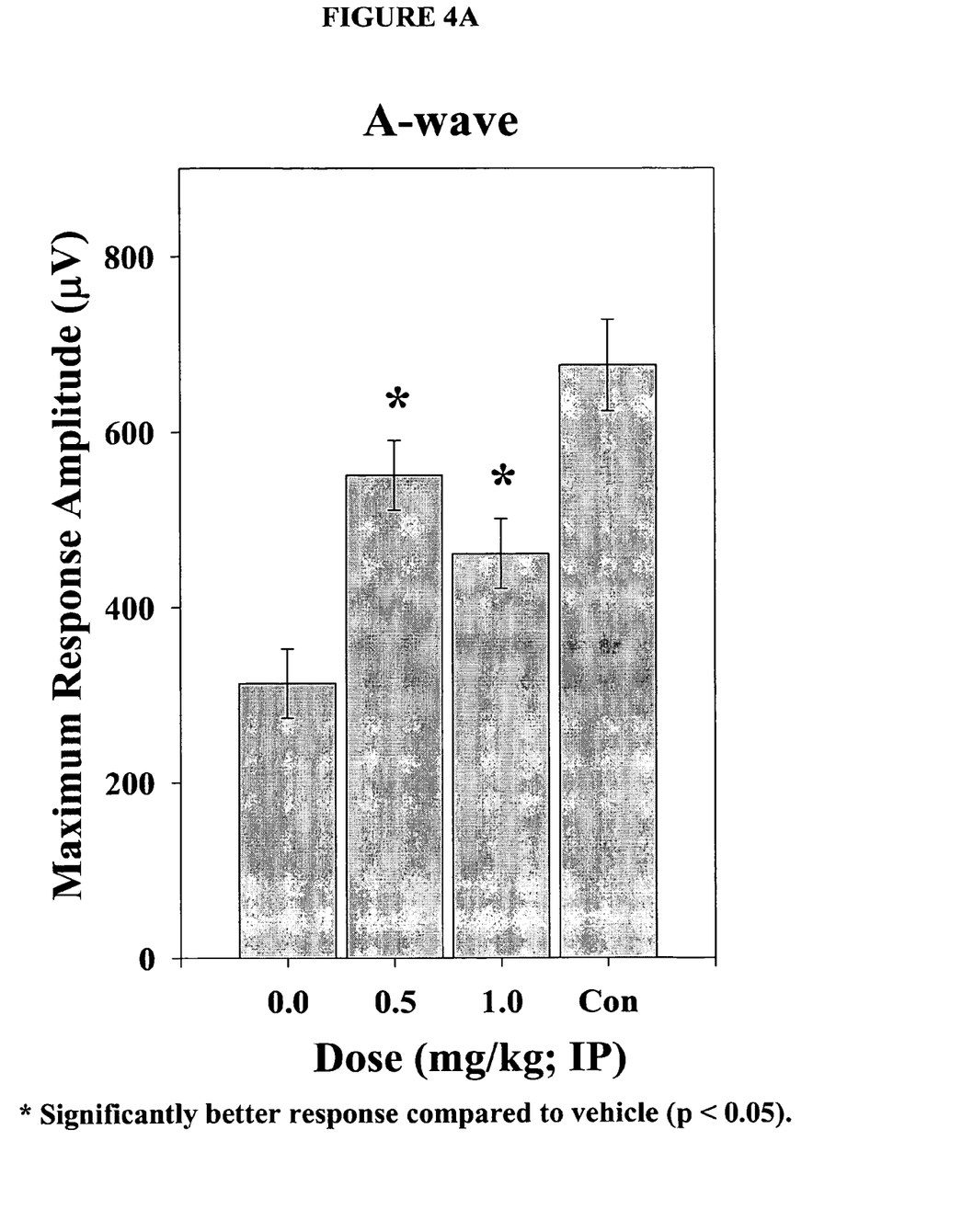
FIGS. 4A and 4B show the preservation of the ERG a- and b-wave function in rats dosed systemically with SR-57746A and exposed to a severe photo-oxidative insult.
Figure 4B:
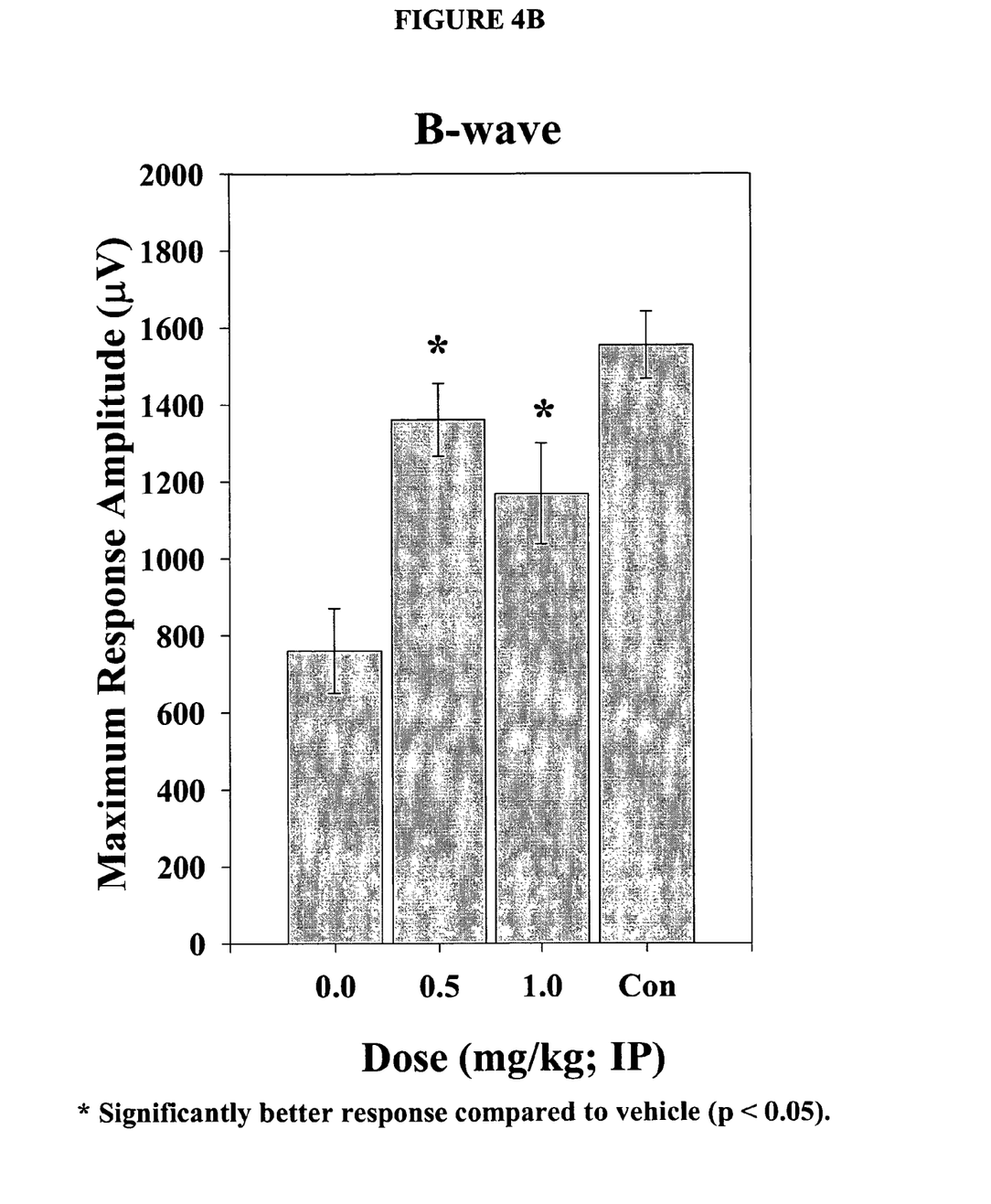

SR-57746A Evaluation Results. Significant protection of retinal function was measured in light-exposed rats dosed with SR-57746A (0.5 and 1.0 mg/kg). Maximum a- and b-wave response amplitudes were reduced by 50% in vehicle dosed rats compared to controls (FIGS. 4A and B). Maximum responses were 82% of controls in rats dosed with SR-57746A (0.5 mg/kg) and 70% of normal in rats dosed with 1 mg/kg.

Conclusion. These $5\text{-HT}_{1A}$ agonists (8-OH-DPAT, buspirone, and SR-57746A) demonstrated good potency and efficacy in this oxidative model of retinal degenerative disease. Functional and structural protection were achieved in rats dosed on three consecutive days with a dose as low as 1 mg/kg.

We claim:

1. A method for treating a disorder of the outer retina in a patient suffering from such a disorder, which comprises administering a pharmaceutically effective amount of a compound with $5\text{-HT}_{1A}$ agonist activity to the eye of said patient, wherein the compound is selected from the group consisting of: tandospirone, ziprasidone, repinotan hydrochloride, xaliproden hydrochloride (SR-57746A), buspirone, flesinoxan, 5-{4-[4-(5-cyano-3-indolyl)-butyl]-1-piperazinyl}-benzofuran-2-carboxamide (EMD-68843), bifeprunox mesylate (DU-127090), gepirone, alnespirone, (R)-5,6-dihydro-5-(methylamino)-4H-imidazo[4,5,1-ij]quinolin-2-(1H)-one (Z)-2-butenedioate maleate (PNU-95666), [N-piperonyl-2-amino-1,2,3,4-tetrahydrobenzo(b)thieno(2,3-c)pyridine]-3-carbamide hydrochloride (AP-521), flibanserin, 5-{3-[((2S)-1,4-benzodioxan-2-ylmethy)amino]propoxy}-1,3-benzodioxole HCl (MKC-242), lesopitron, sarizotan hydrochloride, 4-(4-fluorophenil)-1,2,3,6-tentrahydro-1-[4-(1,2,4-triazol-1-il)butyl]pyridine citrate (E-5842), 3-chloro-4-[4-[4-(2-pyridinyl)-1,2,3,6-tetrahydropyridin-1-yl]butyl]-1,4-benzoxazepin-5(4H)-one (SUN-N4057), 1-(4-trifluoromethyl-2-pyridinyl)-4-[4-[2-oxo-1-pyrrolidinyl]]butyl]piperazine (E)-2-butenedioate (Org-13011), and 8-OH-DPAT, and wherein the disorder is selected from the group consisting of: age-related macular degeneration (AMD), retinitis pigmentosa (RP), retinal detachment, retinal tears, macular pucker, ischemia affecting the outer retina, diabetic retinopathy, damage associated with laser therapy (grid, focal, and panretinal) including photodynamic therapy (PDT), retinal trauma, surgical or light-induced iatrogenic retinopathy, and preservation of retinal transplants.

2. The method of claim 1 wherein the disorder is AMD.

3. The method of claim 1 wherein the disorder is selected from the group consisting of RP, and diabetic retinopathy.

4. The method of claim 1, wherein the compound is tandospirone.

5. The method of claim 4, wherein the disorder is AMD.

6. The method of claim 1, wherein the compound is xaliproden hydrochloride.

7. The method of claim 1, wherein the compound is repinotan hydrochloride.

8. The method of claim 1, wherein the compound is buspirone.

9. A method for treating AMD in a patient suffering from AMD, which comprises administering a pharmaceutically effective amount of a compound with $5\text{-}HT_{1A}$ agonist activity to the eye of said patient, wherein the compound is tandospirone.

* * * * *